United States Patent
Bäck et al.

(10) Patent No.: US 10,888,473 B2
(45) Date of Patent: Jan. 12, 2021

(54) ARRAY OF DISPOSABLE PANT-TYPE GENDER-SPECIFIC ABSORBENT ARTICLES

(71) Applicant: Essity Hygiene and Health Aktiebolag, Gothenburg (SE)

(72) Inventors: Lucas Bäck, Gothenburg (SE); Katarina Eriksson, Gothenburg (SE); Anna Klinte Olsson, Gothenburg (SE)

(73) Assignee: ESSITY HYGIENE AND HEALTH AKTIEBOLAG, Göteborg (SE)

( * ) Notice: Subject to any disclaimer, the term of this patent is extended or adjusted under 35 U.S.C. 154(b) by 0 days.

(21) Appl. No.: 16/496,492

(22) PCT Filed: Mar. 28, 2017

(86) PCT No.: PCT/SE2017/050296
§ 371 (c)(1),
(2) Date: Sep. 23, 2019

(87) PCT Pub. No.: WO2018/182470
PCT Pub. Date: Oct. 4, 2018

(65) Prior Publication Data
US 2020/0022850 A1    Jan. 23, 2020

(51) Int. Cl.
*A61F 13/15*    (2006.01)
*A61F 13/20*    (2006.01)
(Continued)

(52) U.S. Cl.
CPC ........ *A61F 13/5519* (2013.01); *A61F 13/491* (2013.01); *A61F 13/496* (2013.01);
(Continued)

(58) Field of Classification Search
CPC .... A61F 13/471; A61F 13/472; A61F 13/491; A61F 13/4915; A61F 13/496;
(Continued)

(56) References Cited

U.S. PATENT DOCUMENTS 8,273,067 B2 * 9/2012 Cohen ................. A61F 13/49
604/385.01
2005/0256757 A1  11/2005 Sierra et al.
(Continued)

FOREIGN PATENT DOCUMENTS

CN    101677879 A    3/2010
CN    102247245 A    11/2011
(Continued)

OTHER PUBLICATIONS

International Search Report and Written Opinion for International Application No. PCT/SE2017/050296, dated Dec. 22, 2017—12 pages.
(Continued)

*Primary Examiner* — Michele M Kidwell
(74) *Attorney, Agent, or Firm* — Buchanan Ingersoll & Rooney P.C.

(57) ABSTRACT

An array of disposable pant-type gender-specific absorbent articles adapted for female and male users is described. The array has a first subarray of absorbent articles including a first size absorbent article adapted for female users and a second size absorbent article adapted for female users. The second size is larger than the first size. The array also has a second subarray of absorbent articles including a third size absorbent article for male users and a fourth size absorbent article adapted for male users. The fourth size is larger than the third size. An array of packages of the array of disposable pant-type gender-specific absorbent articles is also described.

20 Claims, 7 Drawing Sheets

(51) Int. Cl.
*A61F 13/551* (2006.01)
*A61F 13/49* (2006.01)
*A61F 13/491* (2006.01)
*A61F 13/496* (2006.01)
*A61F 13/53* (2006.01)

(52) U.S. Cl.
CPC .... *A61F 13/49015* (2013.01); *A61F 13/4915* (2013.01); *A61F 13/53* (2013.01); *A61F 13/5511* (2013.01); *A61F 2013/49074* (2013.01)

(58) Field of Classification Search
CPC ............ A61F 13/5519; A61F 13/49015; A61F 13/53; A61F 13/5511; A61F 13/494; A61A 2013/49074
See application file for complete search history.

(56) References Cited

U.S. PATENT DOCUMENTS

| | | | |
|---|---|---|---|
| 2005/0256758 A1* | 11/2005 | Sierra | A61F 13/53 604/378 |
| 2005/0287892 A1* | 12/2005 | Fouse | B26D 1/00 442/59 |
| 2006/0069372 A1* | 3/2006 | Chakravarty | A61F 13/15617 604/385.02 |
| 2008/0110782 A1* | 5/2008 | Burgdorf | A61F 13/551 206/438 |
| 2008/0128308 A1* | 6/2008 | Betts | A47F 3/00 206/440 |
| 2008/0275415 A1 | 11/2008 | Wheeler et al. | |
| 2009/0264851 A1* | 10/2009 | Richlen | A61F 13/5519 604/385.28 |
| 2010/0040826 A1* | 2/2010 | Autran | A61F 13/51464 428/113 |
| 2010/0108554 A1 | 5/2010 | Melius et al. | |
| 2015/0082751 A1 | 3/2015 | Nair et al. | |
| 2015/0283004 A1 | 10/2015 | Seitz et al. | |
| 2016/0100999 A1 | 4/2016 | Hamilton et al. | |
| 2017/0246047 A1* | 8/2017 | Ryu | A61F 13/491 |

FOREIGN PATENT DOCUMENTS

| | | | |
|---|---|---|---|
| CN | 106163474 A | 11/2016 | |
| JP | H01-107319 U | 7/1989 | |
| JP | H04-242643 A | 8/1992 | |
| JP | 2010-525853 A | 7/2010 | |
| JP | 2011514178 A | 5/2011 | |
| JP | 2011517985 A | 6/2011 | |
| WO | 03053279 A2 | 7/2003 | |
| WO | 2009094530 A1 | 7/2009 | |
| WO | 2009/128029 A2 | 10/2009 | |
| WO | 2010/052597 * | 5/2010 | ........... A61F 13/472 |
| WO | 2014098683 A1 | 6/2014 | |
| WO | 2015127220 A1 | 8/2015 | |
| WO | 2015130263 A1 | 9/2015 | |
| WO | 2015171384 A1 | 11/2015 | |
| WO | 2017044022 A1 | 3/2017 | |
| WO | 2018106160 A1 | 6/2018 | |

OTHER PUBLICATIONS

Chinese Office Action for Chinese Application No. 201780087062.2, dated Feb. 5, 2020 with translation, 22 pages.
Extended European Search Report for European Application No. 17903978.9, dated Mar. 16, 2020, 4 pages.
Office Action (Notice of Reasons for Rejection) dated Sep. 28, 2020, by the Japanese Patent Office in corresponding Japanese Patent Application No. 2019-553398, and an English Translation of the Office Action. (16 pages).

* cited by examiner

ARRAY OF DISPOSABLE PANT-TYPE GENDER-SPECIFIC ABSORBENT ARTICLES

CROSS REFERENCE TO RELATED APPLICATIONS

This is a U.S. National Phase application of PCT/SE2017/050296, filed Mar. 28, 2017, the disclosure of which is incorporated herein by reference in its entirety for all purposes.

TECHNICAL FIELD

The invention relates to an array of disposable pant-type gender-specific absorbent articles adapted for female and male users. The array comprises a first subarray of absorbent articles including a first size absorbent article adapted for female users and a second size absorbent article adapted for female users, wherein the second size is larger than the first size. The array further comprises a second subarray of absorbent articles including a third size absorbent article for male users and a fourth size absorbent article adapted for male users, wherein the fourth size is larger than the third size.

BACKGROUND

In the field of disposable pant-type absorbent articles there is a general desire to provide absorbent articles with increased comfort and fit as well as discrete underwear-like visual appearance. Due to anatomical differences between men and women it is not always suitable to have only one kind of absorbent articles. However, having different products for males and females requires different manufacturing apparatuses, leading to increased costs if the differences between male and female gender-specific absorbent articles are too many. Thus, further improvements in terms of comfort, fit and discrete underwear-like visual appearance while maintaining a low manufacturing cost is desirable.

SUMMARY

It is an object of the present invention to provide an array of disposable pant-type gender-specific absorbent articles adapted for female and male users addressing the above mentioned desires. This object is achieved at least partly by the features of claim 1. Variations of the invention are found in the dependent claims.

The invention relates to an array of disposable pant-type gender-specific absorbent articles adapted for female and male users. The array comprises a first subarray of absorbent articles including a first size absorbent article adapted for female users and a second size absorbent article adapted for female users, wherein the second size is larger than the first size, a second subarray of absorbent articles including a third size absorbent article for male users and a fourth size absorbent article adapted for male users, wherein the fourth size is larger than the third size. Each absorbent article of the array has a longitudinal direction and a transverse direction and comprises a front panel having a waist edge, a pair of leg edges and a pair of side edges, a back panel having a waist edge, a pair of leg edges, a pair of side edges, and an absorbent insert located mainly in a crotch portion of the absorbent article (1) and being connected to the front and back panels and having an absorbent core with longitudinal core edges, a front core edge and a back core edge. Each absorbent core in the array has a front portion extending in the longitudinal direction from a transverse centre line of the absorbent article to the front core edge and defining a front core area, and a back portion extending in the longitudinal direction from the transverse centre line of the absorbent article to the back core edge and defining a back core area. Each absorbent article in the array has side elastic members extending along the longitudinal core edges. Each absorbent article in the first subarray has a front core area-to-back core area ratio less than 1.2, each absorbent article in the second subarray has a front core area-to-back core area ratio larger than 1.2, and a longitudinal length of the side elastic members extending between the transverse centre line towards the front core edge of each absorbent article of the first subarray is smaller than the longitudinal length of the side elastic members extending between the transverse centre line towards the front core edge of each absorbent article of the second subarray.

One advantage with the invention is that the articles in the first and second subarray are adapted to the anatomy of females and males respectively. Due to the anatomy of male genitalia, the location of urine discharge for male users is not as isolated as it is for female users. Urine discharge for male users can occur over a much greater area than for a female user depending on the orientation of the penis. Also, the orientation of the penis may shift during use of the absorbent product due to movement of the male user. The greater front core area-to-back core area ratio of the articles in the second sub-array ensures that the core has a greater area in a part of the absorbent core where likelihood of urine discharge is greatest. This increases the likelihood that the urine discharge will be absorbed by the core and will not fall outside of the core. The more concentrated and rearwards location of urine discharge for female users allows for a smaller front core area-to-back core area. Moreover, the more front-located positioning of the side elastic members of the absorbent articles of the second subarray enable improved formation of an outwardly protruding bulge in the absorbent core for improved comfort, fit and anti-leakage for male users.

A width of the front panel in the transverse direction of an absorbent article of the first subarray is substantially the same as a width of the front panel in the transverse direction of an absorbent article of the second subarray. Thereby, simplified manufacturing of the array is accomplished because at least one article in the first subarray share substantially the same width of the front panel in the transverse direction as at least one article in the second subarray.

The longitudinal length of the side elastic members extending between the transverse centre line of the absorbent article to the front core edge of the absorbent core of the first subarray may be at least 15% shorter, specifically at least 20% shorter, and more specifically at least 25% shorter, than the longitudinal length of the side elastic members extending between the transverse centre line of the absorbent article to the front core edge of the absorbent core of the second subarray. This feature of the articles of the first and second subarrays adds to the adaptation of the articles in the first subarray to the female anatomy as well as to the adaptation of the articles in the second subarray to the male anatomy.

A total longitudinal length of the side elastic members of the first subarray may be at least 15% shorter, specifically at least 20% shorter, and more specifically at least 25% shorter, than a total longitudinal length of the side elastic members of the second subarray. This feature of the articles of the first and second subarrays adds to the adaptation of the articles in the first subarray to the female anatomy as well as to the adaptation of the articles in the second subarray to the male anatomy.

Each absorbent core in the array may have a front segment with a length in the longitudinal direction which is 30% of the total length of core in the longitudinal direction and extending from a front edge of the core, wherein the area of the front segment of each absorbent article in the second subarray may be at least 1.1 times larger, specifically at least 1.2 times larger, and more specifically at least 1.25 times larger, than the area of the front segment of each absorbent article in the first subarray. One advantage with having a larger area of the front segment of the core of an article in the second subarray than the area of the front segment of the core of an article in the second subarray is that the core of the articles in the second subarray will have a greater area where the likelihood of urine discharge is the greatest. This further increases the likelihood that the urine discharge will be absorbed by the core and will not fall outside of the core.

For each absorbent article in the second subarray, a width of the core at the front core edge in the transverse direction may be smaller than the width of the core in the transverse direction in the rest of the front segment of the core, and, for each absorbent article in the first subarray, the width of the core at the front core edge in the transverse direction may be substantially equal to the width of the core in the transverse direction in the rest of the front segment of the core. This simplifies production of the core and reduces waste during production of the core.

A smallest longitudinal distance between a side edge of the front panel and the oppositely located side edge of the back panel, as measured with non-attached side seams, of each absorbent article in the array may be essentially the same. This simplifies manufacturing of the articles.

All absorbent articles within the first subarray may have substantially identical absorbent inserts. This relates to aspects such as absorbent insert length and width dimensions and/or absorbent core length and width dimensions. This may also relate to aspects such as absorption capacity and/or positioning of leg elastics. Having identical absorbent inserts in all absorbent products within the first subarray enables more cost-effective manufacturing.

All absorbent articles within the second subarray may have substantially identical absorbent inserts. This relates to aspects such as absorbent insert length and width dimensions and/or absorbent core length and width dimensions. This may also relate to aspects such as absorption capacity and/or positioning of leg elastics. Having identical absorbent inserts in all absorbent products within the second subarray enables more cost-effective manufacturing.

Alternatively, the size of the absorbent insert in the longitudinal direction and transverse direction may be substantially the same for all absorbent articles in the array. This further simplifies manufacturing of the articles.

The front and back panels may be joined to each other at opposite side edges by seams forming a waist opening and two leg openings.

Each absorbent article in the array may have a substantially equal longitudinal length between the transverse centre line of the absorbent article and the edge of the absorbent insert in the back portion.

The maximal width of the absorbent core may be between 120-200 mm in the transverse direction and where the minimal width of the absorbent core may be in the range of 60-140 mm, more specifically in the range of 80-130 mm, in the transverse direction.

A front portion of the absorbent insert may be attached to the front panel of the absorbent article and a back portion of the absorbent insert may be attached to the back panel of the absorbent article.

The front and/or back panel may extensively be made of an elastic web material, wherein the elastic web material is made of at least two substantially inelastic sheets of web material laminated together and having an elastic feature sandwiched between said at least two sheets of web material, and wherein the elastic feature is attached to the at least two sheets in a tensioned state in the width direction to provide a web material that is elasticized in the width direction.

The elastic feature may comprise an elastic film extending both in the length direction and width direction, or wherein the elastic feature comprises a plurality of substantially parallel elastic threads.

The front and back panels may be made of individual parts that are mutually interconnected by means of the absorbent insert, or wherein the front and back panels are integral parts of a single-piece chassis made of one piece of web material having cut-out leg openings, wherein the absorbent body is located overlapping a crotch portion of the chassis.

The absorbent articles may be pant diapers or sanitary pants or incontinence pants.

The invention also relates to an array of packages comprising the array of disposable pant-type gender-specific absorbent articles. The first subarray of absorbent articles may include a plurality of first size absorbent articles adapted for female users and packed in a first package, and a plurality of second size absorbent articles adapted for female users and packed in a second package. The second subarray of absorbent articles includes a plurality of third size absorbent articles for male users and packed in a third package, and a plurality of fourth size absorbent articles adapted for male users and packed in a fourth package. Each of the first to fourth packages in the array of packages comprises an external marking indicating the size and/or suitable gender of the disposable pant-type absorbent articles therein.

DETAILED DESCRIPTION OF PARTICULAR EMBODIMENTS

Various aspects of the disclosure will hereinafter be described in conjunction with the appended drawings to illustrate and not to limit the disclosure, wherein like designations denote like elements, and variations of the described aspects are not restricted to the specifically shown embodiments, but are applicable on other variations of the disclosure. Sizes and distances are not necessarily to scale but may be exaggerated for illustrative purposes.

Figure 1A:
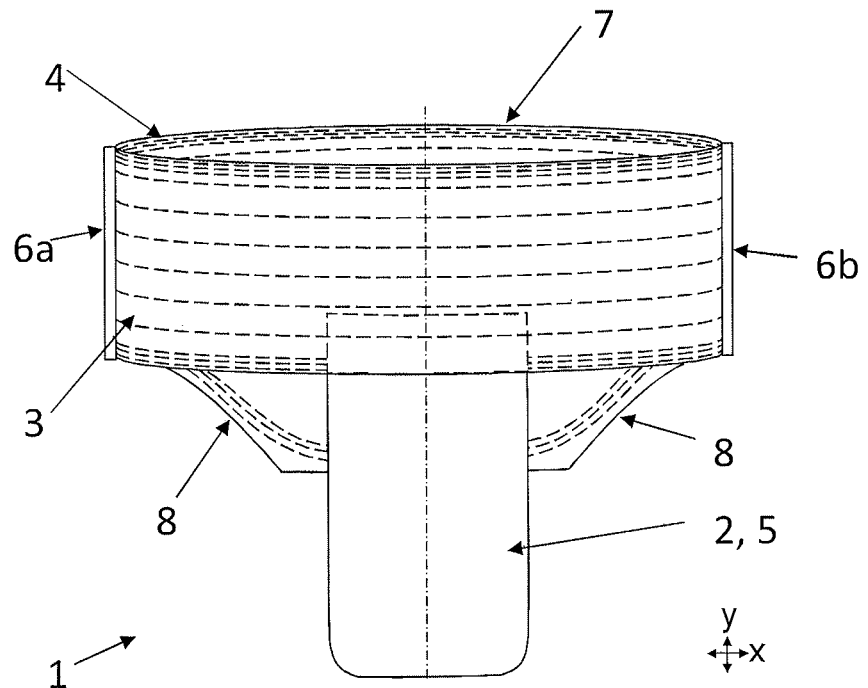
FIG. 1a shows a perspective view of an absorbent article according to the disclosure.

In FIG. 1a of the drawings an example embodiment of a disposable pant-type absorbent article 1 specially adapted for an adult user is schematically illustrated in an assembled and ready-to-use state. The pant-type absorbent article 1 is for example pant diaper, a sanitary pant or an incontinence pant adapted for use of an adult female or male user. The pant-type absorbent article 1 according to the example embodiment of FIG. 1a comprises a dual-piece chassis having a front panel 3, a back panel 4 and an absorbent insert 2 located mainly in a crotch portion of the absorbent article 1 and connected to interior side of the front and back panels 3, 4 for bridging the gap between the front and back panels 3, 4. The absorbent insert 2 comprises an absorbent core 5 for absorbing body fluid.

In short, manufacturing of the pant-type absorbent article 1 is performed by first manufacturing two parallel continuous strips of laminated elastic web material that should form the front and rear body panels 3, 4 of the finished absorbent article 1.

Manufacturing of the laminated elastic web material of the front and rear body panels 3, 4 are typically performed by feeding a first and a second continuous substantially non-elastic sheet of web material, such as for example a substantially non-elastic nonwoven material, along a machine direction, while simultaneously feeding a plurality of continuous elastic threads arranged parallel with one another. Subsequently, the first and second sheets of web material are joined to each other with a plurality of continuous elastic threads located between the first and second sheets.

The elastic threads are attached to the first and second sheets in a tensioned state and parallel with the web material. Elastic threads arranged parallel with the machine direction, i.e. in the transverse direction X, may for example have adhesive applied thereto before being fastened in a tensioned state to the web material. Alternatively, the web material itself may have adhesive applied to it for securing the elastic threads thereto. The latter is particularly advantageous when the elastic threads exhibit a curved orientation over the transverse length of the absorbent article 1. The finished laminated elastic web will consequently gather when allowing the elastic threads to return to their natural state.

However, while still keeping the elastic threads in tensioned state the method further comprises a step of placing a finished absorbent insert 2 in the gap between the two parallel continuous strips of laminated elastic web, such that the absorbent insert 2 partly overlaps with the both said strips, and subsequently securing the absorbent insert 2 to said strips. The absorbent insert 2 is thus manufactured separately from the front and back panels 3, 4 and subsequently placed and fastened to said body panels 3, 4 in a suitable manufacturing step.

The manufacturing method may optionally include the step of providing a flat front and/or flat back design. This would involve having the elastic threads free of adhesive in a central area of the front and/or rear body panel and performing an interrupting operating of the elastic threads located in the central portion of the front and/or rear body panel, such that the portion of the elastic threads located in the central portion of the front and/or rear body panel 3, 4 and are free from adhesive are allowed to return to their natural, un-tensioned, state without exerting a gathering effect on the surrounding web material, thereby creating a flat area at a desired region of the front and/or rear body panel 3, 4. Such a flat area is typically desirable in the area where the absorbent core 5 overlaps the front and/or rear body panels 3, 4 because the gathering effect of active elastic threads on the absorbent core 5 may be deemed having a negative effect on the absorption capacity of the absorbent core 5. Alternatively, the elastic means in the second location might have been applied as elastic threads crossing the pant article 1 in the transverse direction that have been deactivated or cut in the area of the core 5. Also the elastic means in the lower area of the front section have also been deactivated similarly. One way of deactivating elastic threads is disclosed in application No. PCT/SE2016/051221.

After securing the absorbent insert 2 to the two parallel continuous strips of laminated elastic web the entire continuous material band is folded at a fold line extending substantially in the transverse direction X of the absorbent insert 2, such that the two parallel continuous strips of laminated elastic web becomes superposed after folding. Thereafter the two parallel continuous strips of laminated elastic web are joined to each other at discrete locations at predetermined fixed intervals along the material band using for example ultrasonic welding, to form side seams 6a, 6b of the finished absorbent article 1. Consequently, side edges of the front panel 3 are permanently attached to opposite side edges of the back panel 4 to form side seams 6a, 6b of the finished and assembled absorbent article 1, thereby also defining a waist-opening 7 and a pair of leg-openings 8.

In a final step the continuous material band is cut in, a machine cross direction in the area in or adjacent to the side seams 6a, 6b to transform the folded continuous material band into individual absorbent articles 1. When the laminated elastic web material of the front and back panels 3, 4 is no longer held in stretched state in the transverse direction X the sandwiched elastic threads will cause the web material to gather, i.e. to contract in the transverse direction X and to form small undulations in the laminated elastic web material. An example manufacturing process for such an elastic web material is described more in detail in document WO 2014/098683 A1, which is referred to in its entirety.

Figure 1B:
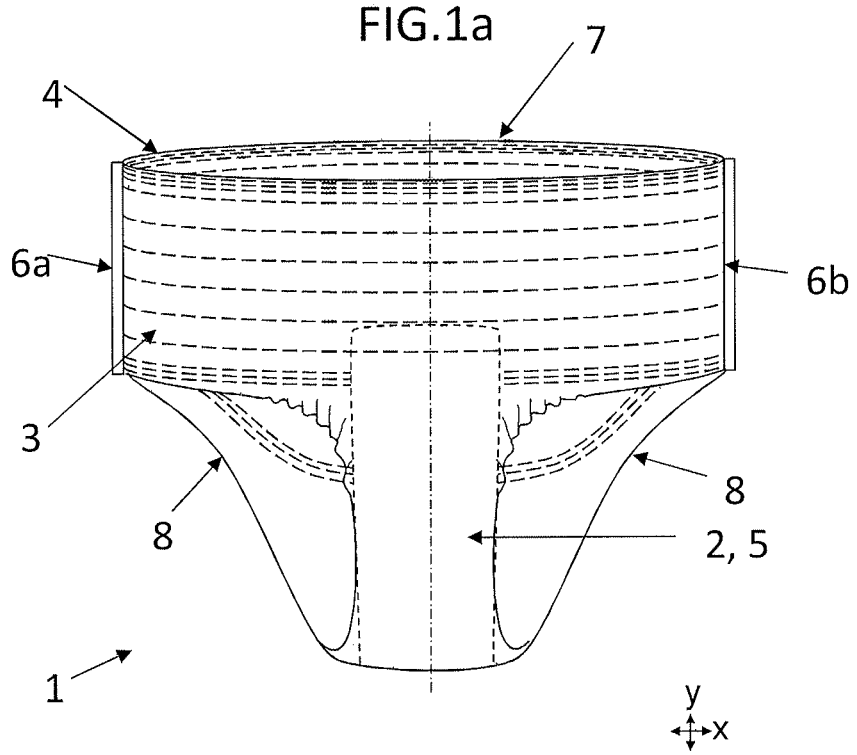
FIG. 1b shows a perspective view of an alternative absorbent article according to the disclosure.

In FIG. 1b of the drawings a second example embodiment of a disposable pant-type absorbent article 1 specially adapted for an adult female or male user is schematically illustrated in an assembled and ready-to-use state. The difference between the articles in FIGS. 1a and 1b is that the article 1 in FIG. 1b is a one-piece chassis, i.e. the front and back panels 3, 4 belong to the same single-piece web material that has an integrally formed crotch region interconnecting the front and back panels 3, 4.

Figure 2:
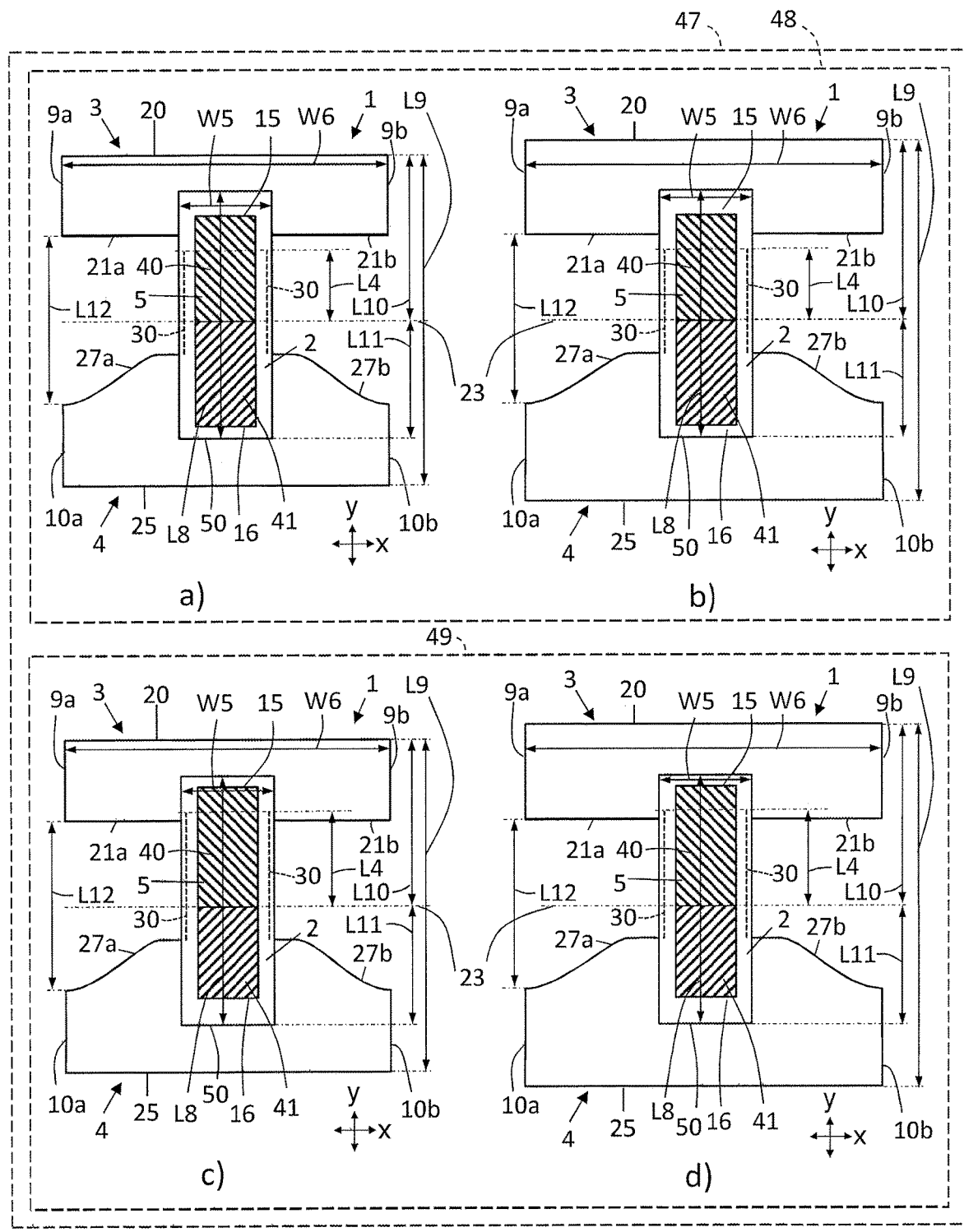
FIGS. 2a-2d shows an array of absorbent articles of various sizes of the first and second subarrays in disassembled flat state.

FIG. 2 schematically shows an array 47 of absorbent articles 1 of various sizes of the first and second subarrays 48, 49 in a flat, extended and stretched-out state. In particular, FIG. 2a shows a first size absorbent article 1 adapted for female users, FIG. 2b shows a second size absorbent article 1 adapted for female users, FIG. 2c shows a third size absorbent article 1 adapted for male users and FIG. 2d shows a fourth size absorbent article adapted for male users are shown in a flat, non-assembled state, and without opposite side edges 9a, 9b, 10a, 10b of the front and back panels 3, 4 being attached to each other in side seams 6a, 6b. This may for example be realised by reviewing absorbent articles before finalising the side seams 6a, 6b during manufacturing of the articles, or by breaking the side seams 6a, 6b of a finished absorbent article 1 of FIG. 1a or 1b and unfolding the pant-type absorbent article 1 into a flat state. The pant-type absorbent article 1 comprises, in an unfolded and flat state, a longitudinal direction Y that is substantially parallel with a direction of elongation of the absorbent insert 2. The transverse direction X is perpendicular to the longitudinal direction Y.

The pant-type absorbent articles 1 of the array 47 according to example embodiment of FIG. 2 comprises a front panel 3 having a waist edge 20, a pair of leg edges 21a, 21b and a pair of side edges 9a, 9b. The front panel 3 has a substantially rectangular shape, and the width W6 of the front panel 3 in the transverse direction X is typically in the range of about 550-790 mm and the total length of the front panel 3 in the longitudinal direction Y is typically in the range of about 110-400 mm, depending on the size of the absorbent article 1.

A rectangular shape front panel 3 enables cost-efficient manufacturing because elastic threads applied to the front panel 3 for elasticising the front panel 3 may also be arranged in the transverse direction X of the absorbent article 1, i.e. along the machine direction in the manufacturing machine. Straight elastic threads require less complex manufacturing equipment and the adhesive for securing the elastic threads may be supplied directly on the elastic threads before laminating the sheets of web material and elastic threads together to form body panels. Moreover, the rectangular shaped front panel 3 also enables manufacturing with low level of scrap material caused for example by cutting out complex two-dimensional shapes from a sheet of laminated web material. In FIGS. 2a-2d, the elastic threads are not shown.

The pant-type absorbent articles 1 of the array 47 according to example embodiment of FIG. 2 also comprises a back panel 4 having a waist edge 25, a pair of leg edges 27a, 27b and a pair of side edges 10a, 10b. The back panel 4 may have a shape composed of a substantially rectangular shaped main section intended to be located towards a waist of a user and a substantially trapezoid shaped buttocks-covering section intended to be located towards a crotch of a user. A certain level of variations in said schematic geometry is of course possible. For example, the side edges of said sections may for example be non-linear, the corners may be more rounded, the total width of the buttocks-covering section in the transverse direction X may be smaller than the total width of the main section in the transverse direction X, etc. A substantially trapezoid shaped buttocks-covering section provides improved fit and comfort to a user, as well as improved underwear-like visual appearance.

In the example embodiments of FIGS. 1a to 2d the main section of the back panel 4 has shape that substantially corresponds to the rectangular-shaped front panel 3. In other words, the length of the main section of the back panel 4 in the longitudinal direction Y is substantially equal to the length of the rectangular-shaped front panel 3 in the longitudinal direction Y, and the width of the main section of the back panel 4 in the transverse direction X is substantially equal to the width W6 of the rectangular-shaped front panel 3 in the transverse direction X.

According to a further example embodiment, the length of the main section of the back panel 4 in the longitudinal direction Y may be substantially equal to the length of the side seam 6a, 6b in the longitudinal direction Y.

The absorbent article 1 of FIGS. 2a-2d has an absorbent insert 2 located mainly in a crotch portion of the absorbent article 1 which is connected to the front and back panels 3, 4. The absorbent article 1 has side elastic members 30 extending along the longitudinal core edges 14. The side elastic members 30 may be attached to the core 5, and/or to the insert 2 in a region between a longitudinal edge of the insert and a longitudinal edge of the core 5, and/or to an underlying chassis material integrally formed with the front and/or back panel 3, 4. The side elastic members 30 are arranged to provide a side gathering effect along the transverse sides of the front segment 17 of the core 5. A gathering effect means that the absorbent core 5 within the region of the side elastic member 30 may contract in the direction of extension of the side elastic members 30. This contraction effect of the material of the absorbent article 1 along the transverse sides of a front segment 17 will assist in shaping the absorbent core 5 in the absorbent article 1, and thus generating a more comfortable and leakage secure absorbent article 1.

Inserts 2 are typically manufactured from a long continuous web, wherein absorbent cores and side elastic members 30 are positioned on the web substantially parallel with the longitudinal direction of the continuous web, and wherein individual insert 2 are formed by cutting the continuous web perpendicular to the longitudinal direction of the continuous web. The side elastic members 30 consequently typically extend along the entire length of the insert 2 during manufacturing but since the side elastic members 30 typically are not secured to the material of the insert 2 along the entire longitudinal length end portions of the side elastic members 30 will typically snap-back upon cutting the continuous web into individual inserts 2. The length of the side elastic members 30 herein refers to the active portion of the side elastic members 30, i.e. the portion of the side elastic members 30 that exerts a gathering effect on the insert material in a natural state of the absorbent article 1. The snap-back portions of the side elastic members 30 herein do not form part of the length of the side elastic members 30.

Each elongated side elastic member 30 may include one or more individual elastic threads, such as for example two, three or four elastic threads placed parallel to each other and with a gap between each other. The total length of the side elastic member 30 in the longitudinal direction Y of each absorbent article in the array 47 may be in the range of 4-20 centimetres, specifically 5-15 centimetres, and more specifically 5-10 centimetres.

The absorbent core 5 has a front portion extending in the longitudinal direction Y from a transverse centre line 23 of the absorbent article 1 to the front core edge 15 and defining a front core area 40, and a back portion extending in the longitudinal direction Y from the transverse centre line 23 of the absorbent article 1 to a back core edge 16 of the absorbent core 5 and defining a back core area 41. The transverse centre line 23 extends in the transverse direction X and a longitudinal distance L10 from the waist edge 20 of the front panel 3 to the transverse centre line 23 is 50% of the total longitudinal length L9 of the absorbent article measured from the waist edge 20 of the front panel 3 to the waist edge 25 of the back panel 4.

As described above, one objective with the present disclosure is to provide an array of gender-specific absorbent products in at least two sizes, for the purpose of providing absorbent articles with increased comfort and fit as well as discrete underwear-like visual appearance, while taking into account anatomical differences between men and women and the need for individual sizes, and while also maintaining a low manufacturing cost. The present disclosure provides a solution where two different absorbent article features are adapted to enables the absorbent articles to have better fit to for each gender, wherein said two absorbent article features are longitudinal position of side elastic members 30 and a front/back area-distribution of the absorbent core. These two absorbent article features combined have shown to be important and have a significant effect when adapting absorbent articles to each specific gender.

In detail, more forward located side elastic members 30 have shown to enable improved outward bulge-forming of the absorbent core in the area of male genitals, thereby enabling improved comfort, fit and leakage protection. Correspondingly, more rearwards located side elastic members 30 have shown to enable improved comfort, fit and leakage protection for female users. Moreover, due to the more forwards oriented location of the male urethral opening compared with females, an increased proportion of the absorbent core area at the front of the absorbent article enables improved urine absorption of male urination, whereas an increased proportion of the absorbent core area towards the back enables improved urine absorption of female urination.

Furthermore, for maintaining a low manufacturing cost of the array of absorbent articles the size of an absorbent article feature is identical for at least one absorbent product in the first subarray 48 and for at least one absorbent product in the second subarray 49. For example, the width W6 of the front panel 3 in the transverse direction X of an absorbent article 1, or the total length L9 in the longitudinal direction Y of the absorbent article 1, may be substantially identical for at least one absorbent product in the first subarray 48 and for at least one absorbent product in the second subarray 49.

Manufacturing of various types and sizes of absorbent articles on a single manufacturing line requires a certain degree of adaption of the manufacturing line, such as for example taking into account absorbent product specific sizes. The width of the front panel 3 is consequently an important manufacturing parameter and by using substantially the same width for two different articles in the array the manufacturing process can be simplified due to reduced need for adjustment of the manufacturing line for each individual type of absorbent article. A small deviation in width of the front panel 3 between the two different articles in the array can for example exist to due small dimensional variations in the absorbent articles caused by manufacturing variations and tolerances. This manufacturing-caused dimensional variation is typically less than 2% of any specific dimension.

An example embodiment of an array 47 according to the present disclosure is schematically shown in FIG. 2. The array 47 comprises a first subarray 48 of absorbent articles 1 including a first size absorbent article 1 adapted for female users, as shown in FIG. 2a, and a second size absorbent article 1 adapted for female users, as shown in FIG. 2b, wherein the second size is larger than the first size. The difference in size is reflected in increased width W6 and increased total length L9 of the larger absorbent article. Each absorbent article 1 within the first subarray may however according to an example embodiment have identical absorbent inserts 2 and absorbent cores 5.

The array 47 further comprises a second subarray 49 of absorbent articles 1 including a third size absorbent article 1 for male users, as shown in FIG. 2c, and a fourth size absorbent article 1 adapted for male users, as shown in FIG. 2d, wherein the fourth size is larger than the third size. The difference in size is reflected in increased width W6 and increased total length L9 of the larger absorbent article. Each absorbent article 1 within the second subarray may however according to an example embodiment have identical absorbent inserts 2 and absorbent cores 5.

For the absorbent article 1 of the first subarray 48, i.e. for example according to the absorbent articles of the embodiment of FIGS. 2a and 2b, the longitudinal length L4 of the side elastic members 30 extending in the area between the transverse centre line 23 of the absorbent article 1 and the front core edge 15 is smaller than the longitudinal length L4 of the side elastic members 30 extending in the area between the transverse centre line 23 of the absorbent article 1 and the front core edge 15 of the second subarray, i.e. the articles 1 of FIGS. 2c and 2d. The longitudinal length L4 of the side elastic member 30 for an article 1 adapted for females may be in the range of 200-400 mm. The longitudinal length L4 of the side elastic member 30 for an article 1 adapted for males may be in the range of 250-450 mm.

The longitudinal length L4 of the side elastic members 30 extending between the transverse centre line 23 towards the front core edge 15 of each absorbent article 1 of the first subarray 48 is at least 15% shorter, specifically at least 20% shorter, and more specifically at least 25% shorter, than the longitudinal length L4 of the side elastic members 30 extending between the transverse centre line 23 towards the front core edge 15 of each absorbent article 1 of the second subarray 49.

The side elastic member 30 may extend any suitable length along the longitudinal core edges 14. For example, the side elastic member 30 may extend from the back portion of the core 5 towards the front core edge 15. For each absorbent article in the second subarray 49 the longitudinal distance from the front core edge 15 of the absorbent core 5 to a front edge of the side elastic member 30 may be less than 50 millimetres, and specifically less than 30 millimetres. The side elastic members 30 may even extend beyond the front core edge 15 of the absorbent core 5 towards the front panel waist edge 20 of the absorbent article 1. For each absorbent article in the first subarray 48 the longitudinal distance from the front core edge 15 of the absorbent core 5 to a front edge of the side elastic member 30 may be less than 140 millimetres, and specifically less than 100 millimetres.

As schematically shown in FIGS. 2a and 2b, the first and second size absorbent articles 1 of the first subarray 48 has a front core area-to-back core area ratio less than 1.2. For example, the first and second size absorbent articles 1 of the first subarray 48 may have a front core area-to-back core area ratio of about 1.0 as shown on FIGS. 2a and 2b. This ratio corresponds to a front core area 40 of about the same size as the back core area 41.

The absorbent articles 1 of the first subarray 48 may for example have a front core area-to-back core area ratio in the range of about 0.9-1.2.

As schematically shown in FIGS. 2c and 2d, the first and second size absorbent articles 1 of the second subarray 49 has a front core area-to-back core area ratio larger than 1.2. For example, the first and second size absorbent articles 1 of the second subarray 49 may have a front core area-to-back core area ratio of about 1.3 as shown in FIGS. 2c and 2d. In FIGS. 2c and 2d, the core 5 is located relatively more towards the waist edge 20 of the front panel 3 such that the front core area 40 is larger than the back core area 41.

The absorbent articles 1 of the second subarray 49 may for example have a front core area-to-back core area ratio in the range of about 1.2-1.5.

As stated above, the second size absorbent article is larger than the first size absorbent article, and the fourth size absorbent article is larger than the third size absorbent article. This difference in size may be accomplished by varying the total length L9 and the total width W6 of the absorbent articles 1. The total length L9 of an absorbent article is typically varied by varying the length of the front and/or back panel 3, 4 in the longitudinal direction Y.

As schematically shown in FIG. 2, the total length L9 of the first size absorbent article 1 in FIG. 2a is shorter than the total length L9 of the second size absorbent article 1 in FIG. 2b. Similarly, the total length L9 of the third size absorbent article 1 in FIG. 2c is shorter than the total length L9 of the fourth size absorbent article 1 in FIG. 2d.

The total length L9 of one of the first and second size absorbent articles 1 is however the same as the total length L9 of one of the third and fourth size absorbent articles 1 in order to simplify production. In FIG. 2, the total length L9 of the first size absorbent articles 1 is the same as the total length L9 of the third size absorbent article 1, and the total length L9 of the second size absorbent article 1 is the same as the total length L9 of the fourth size absorbent article 1.

As schematically shown in FIG. 2, the width W6 of the front panel 3 of the first size absorbent article 1 in FIG. 2a is shorter than the width W6 of the second size absorbent article 1 in FIG. 2b. Similarly, the width W6 of the third size absorbent article 1 in FIG. 2c is shorter than the width W6 of the fourth size absorbent article 1 in FIG. 2d.

The width W6 of one of the first and second size absorbent articles 1 is the same as the width W6 of one of the third and fourth size absorbent articles 1 in order to simplify production. In FIG. 2, the width W6 of the first size absorbent articles 1 is the same as the width W6 of the third size absorbent article 1, and the width W6 of the second size absorbent article 1 is the same as the width W6 of the fourth size absorbent article 1.

Moreover, for further enabling cost-efficient manufacturing, a smallest longitudinal distance L12 between the side edge 9a, 9b of the front panel 3 and an oppositely located side edge 10a, 10b of the back panel 4 of each absorbent article 1 in the array may be essentially the same. Using the same smallest longitudinal distance L12 between the side edge 9a, 9b of the front panel 3 and an oppositely located side edge 10a, 10b of the back panel 4 in each absorbent article 1 in the array less adjustments of the manufacturing line need to be performed when changing manufacturing from a first type of absorbent article to a another type.

Moreover, for further enabling cost-efficient manufacturing, the length L8 of the absorbent insert 2 in the longitudinal direction Y and/or width W5 of the absorbent insert 2 in the transverse X direction may be the same for all absorbent articles 1 in the array. Using the length L8 and width W5 in all inserts enable significant manufacturing-cost savings. For example, manufacturing equipment for manufacturing, transporting and placing the inserts on the continuous sheets of web that subsequently forms the front and back panels 3, 4 can be simplified and less variants are needed.

For still further enabling cost-efficient manufacturing, each absorbent article 1 in the array may have a substantially equal longitudinal length L11 between the transverse centre line 23 of the absorbent article 1 and the back edge of the insert 2 in the back portion. The size and form of the core 5 may differ as seen for instance in FIGS. 2a-2d. Having substantially equal longitudinal length L11 between the transverse centre line 23 of the absorbent article 1 and the back edge of the insert 2 in all absorbent articles in the array 47 enables increased flexibility for manufacturing different sizes and different gender-specific absorbent articles in the same manufacturing line while still providing low-cost manufacturing.

Figure 3:
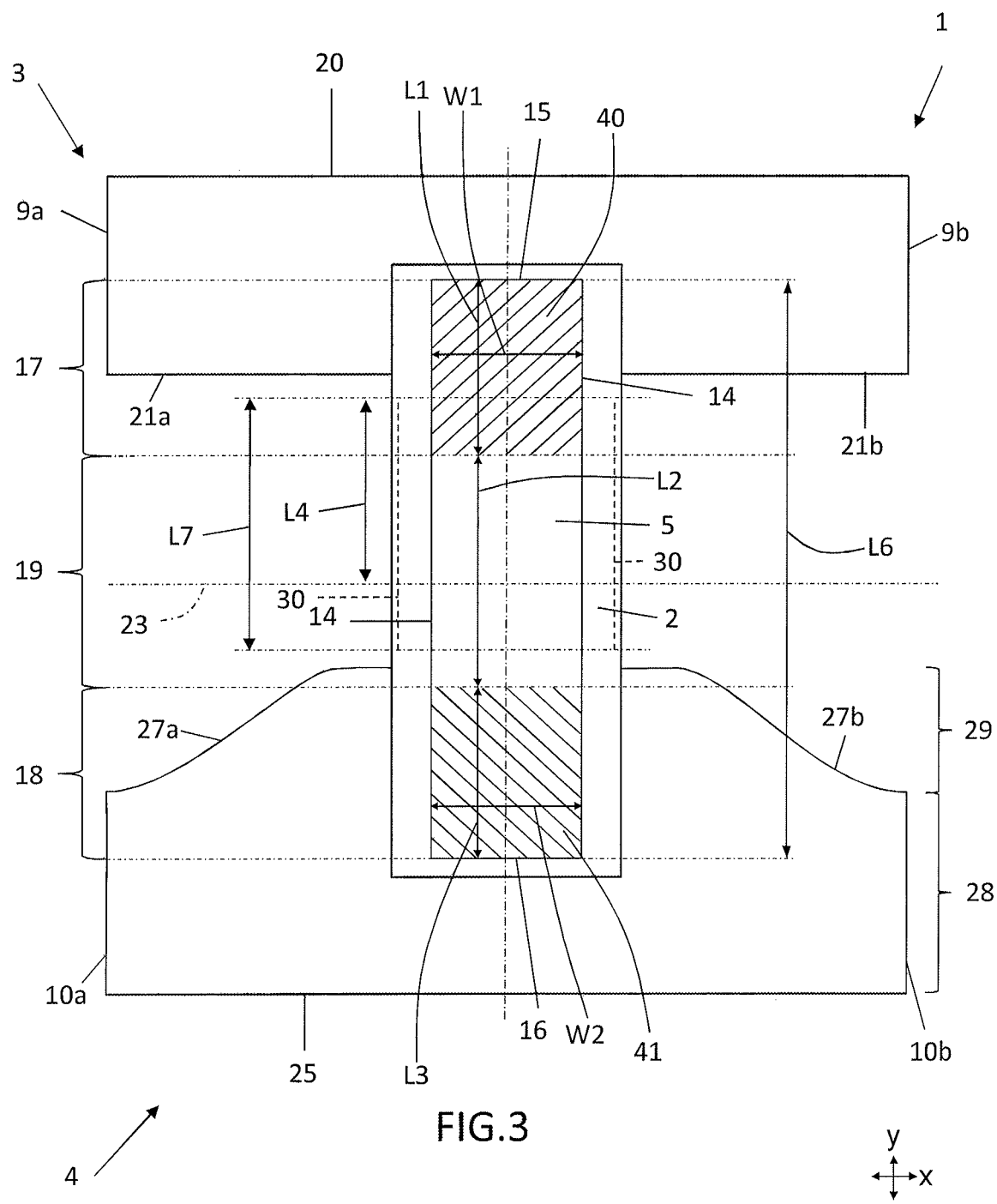
FIG. 3 shows an absorbent article of FIG. 1 in disassembled flat state adapted for a female user.

FIG. 3 of the drawings show an example embodiment of a disposable pant-type absorbent article 1 of the first sub-array 48 adapted for a female user. The pant-type absorbent article 1 is here schematically illustrated in flat, non-assembled state. The features shared with the article 1 of FIGS. 2a-2d have the same reference numbers. The pant-type absorbent article 1 comprises, in an unfolded and flat state, a longitudinal direction Y that is substantially parallel with a direction of elongation of the absorbent insert 2. The transverse direction X is perpendicular to the longitudinal direction Y. The characteristics, such as the materials and the layout of the elastic regions of the absorbent article 1 of FIG. 3 are the same as of the absorbent article 1 of FIG. 2, unless otherwise described below.

The article 1 has an absorbent insert 2 located mainly in a crotch portion of the absorbent article 1 which is connected to the front and back panels 3, 4. The insert 2 comprises an absorbent core 5. The core 5 has a front segment 17 with a length L1 in the longitudinal direction Y which is 30% of the total length L6 of core 5 in the longitudinal direction Y and extending from the front core edge 15, a back segment 18 with a length L2 in the longitudinal direction Y which is 30% of the total length L6 of core 5 in the longitudinal direction Y and extending from a back core edge 16, and a middle segment 19 with a length L3 in the longitudinal direction Y which is 40% of the total length L6 of core 5 in the longitudinal direction Y and being located between the front and back segments 17, 18. In the example embodiment of FIG. 3, the core 5 has an essentially uniform width W1 in the front segment 17 and a uniform width W2 in the back segment 18 and also in the middle segment 19, wherein the width is the same in all segments 17-19.

The core 5 also has side elastic members 30 extending along the longitudinal core edges 14. Side elastic members 30 with a total length L7 are arranged to provide a side gathering effect along the longitudinal sides 14 of the core 5. A gathering effect means that the absorbent core 5 within the region of the side elastic member 30 may contract in the direction of extension of the side elastic members 30. This contraction effect of the material of the absorbent article 1 along the transverse sides of a front segment 17 will assist in shaping the absorbent core 5 in the absorbent article 1, and thus generating a more comfortable and leakage secure absorbent article 1.

A total longitudinal length L7 of the side elastic members 30 of each absorbent article 1 of the first subarray 48 is at least 15% shorter, specifically at least 20% shorter, and more specifically at least 25% shorter, than a total longitudinal length L7 of the side elastic members 30 of each absorbent article 1 of the second subarray 49.

The side elastic member 30 may extend from the back or middle segment 18, 19 towards the front edge 15 of the absorbent core 5.

For the absorbent articles 1 of the first subarray, i.e. the articles adapted for females, the longitudinal length L4 of the side elastic members 30 extending between the transverse centre line 23 of the absorbent article 1 to the front core edge of the absorbent core 5 is smaller than the longitudinal length L4 of the side elastic members 30 extending between the transverse centre line 23 of the absorbent article 1 to the front core edge of the absorbent core 5 of the second subarray.

Figure 4:
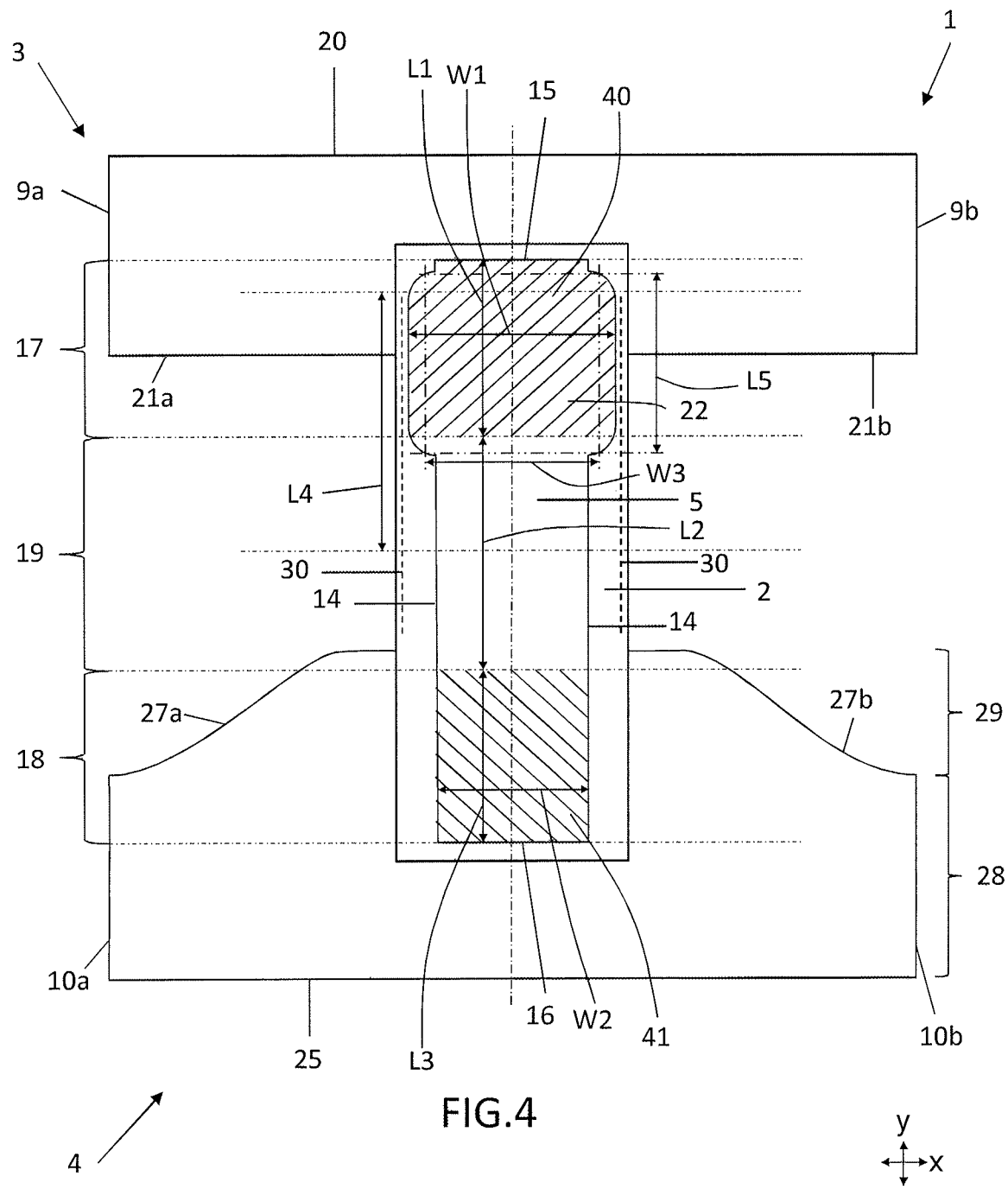
FIG. 4 shows an absorbent article of FIG. 1 in disassembled flat state adapted for a male user.

In FIG. 4 of the drawings an example embodiment of a disposable pant-type absorbent article 1 of the second sub-array 49 adapted for a male user is schematically illustrated in flat, non-assembled state. The features shared with the article 1 adapted for a female user of FIG. 3 have the same reference numbers. The pant-type absorbent article 1 comprises, in an unfolded and flat state, a longitudinal direction Y that is substantially parallel with a direction of elongation of the absorbent insert 2. The transverse direction X is perpendicular to the longitudinal direction Y. The characteristics, such as the materials and the layout of the elastic regions of the absorbent article 1 of FIG. 4 are the same as of the absorbent article 1 of FIG. 3, unless otherwise described below.

The core 5 has a wide portion 22 in the front segment 17. The wide portion 22 has a width W1 in the transverse direction X that is at least 1.1 times greater than the maximal width W2 in the transverse direction X of the core 5 in the back segment 18. In other words, all parts of the front segment 17 that has a transverse width W1 that is 1.1 times greater or more than the maximal transverse width W2 of the core 5 in the back segment 18 defines one or more wide portions 22. The transverse width W1 may thus vary over a length L5 of the wide portion 22 and is not necessarily constant. In fact, the transverse width W1 tend to vary over the length L5 of the wide portion 22 as soon as the front segment 17 has a more rounded and less rectangular outer shape.

The length L5 is defined as the length of the wide portion 22 where the width W1 is 1.1 times greater, or more, than the maximal transverse width W2 of the core 5 in the back segment 18. In FIG. 2 the limit width that is exactly 1.1 times greater than the maximal transverse width W2 of the core 5 in the back segment 18 is marked with W3. The longitudinal length L5 of the wide portion 22 is consequently in FIG. 2 defined by the intersection of the longitudinal core edges 14 with longitudinal lines defined by width W3 and centred around a longitudinal centre line of the absorbent article 1.

The wide portion 22 may extend down into the middle segment 19. The wide portion 22 typically extends over less than 50%, specifically less than 35%, and more specifically less than 20% of the middle segment 19.

The core 5 typically comprises a single wide portion 22 located mainly over the front segment 17.

Generally, for an article 1 adapted for a male user, the area of the front segment 17, i.e. the front core area 40, is more than 1.2 times larger the area of the back segment 18, i.e. the back core area 41.

The core 5 also has side elastic members 30 extending along the longitudinal core edges 14. The side elastic members 30 are arranged to provide a side gathering effect along the transverse sides of the front segment 17 of the core 5. A gathering effect means that the absorbent core 5 within the region of the side elastic member 30 may contract in the direction of extension of the side elastic members 30. This contraction effect of the material of the absorbent article 1 along the transverse sides of a front segment 17 will assist in shaping the absorbent core 5 in the absorbent article 1, and thus generating a more comfortable and leakage secure absorbent article 1.

The longitudinal distance from a front edge 15 of the absorbent core 5 to the edge of the side elastic member 30 may be less than 50 millimetres, and specifically less than 30 millimetres. The side elastic members 30 may even extend beyond the front edge 15 of the absorbent core 5 towards the front panel waist edge 20 of the absorbent article 1. The side elastic members 30 may be attached to a chassis of the absorbent article 1, and/or to transverse sides of the insert 2, and/or to the transverse sides of the absorbent core 5.

Each elongated side elastic member 30 may include one or more individual elastic threads, such as for example two, three or four elastic threads placed parallel to each other and with a gap between each other. The length L7 of the side elastic member 30 in the longitudinal direction Y may be in the range of 15-45 centimetres, specifically 20-40 centimetres, and more specifically 25-35 centimetres.

Figure 5:
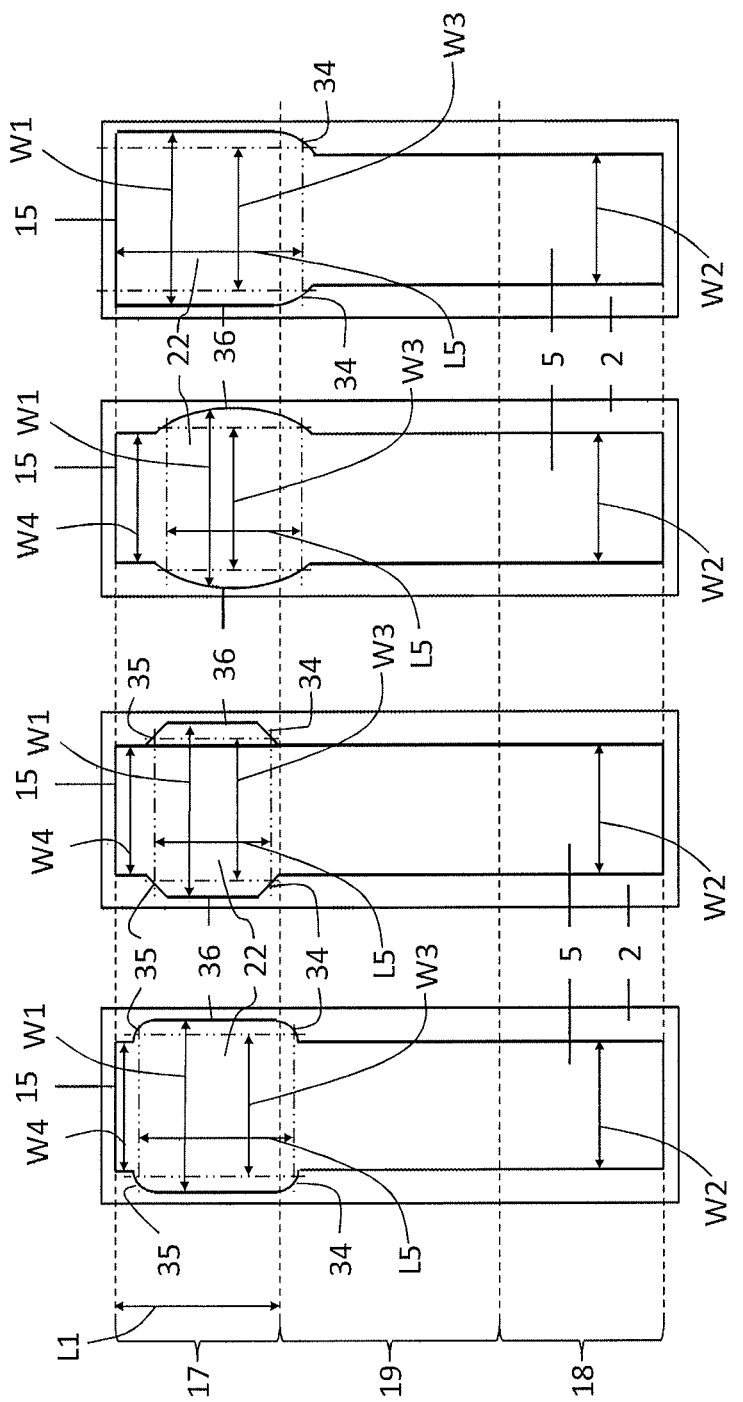
FIGS. 5a-5d shows examples of core shapes of the articles adapted for male users according to the disclosure.

FIGS. 5a-5d shows alternative design embodiments of the core 5, wherein the wide portion 22 in the front segment 17 of the core 5 of the article 1 is adapted for a male of FIG. 3. FIG. 5a shows a wide portion 22 having rounded edges forming lower transitions 34 of the wide portion 22 and the remainder of the core 5 in a bottom part of the wide portion 22. A middle part 36 of the wide portion 22 extends between the lower transitions 34 and upper transitions 35 and is essentially straight in a longitudinal direction Y before rounded edges form upper transitions 35 back to a width W4 adjacent the front edge 15 of the core 5 which is narrower than the width W1 of the wide portion 22. The width W3 indicates where the width of the wide portion 22 is at least 1.1 times the maximal transverse width W2 of the core 5 in the back segment 18.

FIG. 5b shows a wide portion 22 with straight lines forming the lower transitions 34 of the wide portion 22 and the remainder of the core 5 in a bottom part of the wide portion 22. A middle part 36 of the wide portion 22 between the lower transitions 34 and upper transitions 35 is essentially straight in a longitudinal direction Y before straight lines form upper transitions 35 back to a width W4 adjacent the front edge 15 of the core 5 which is narrower than the width W1 of the wide portion 22. The width W3 indicates where the width of the wide portion 22 is at least 1.1 times the maximal transverse width W2 of the core 5 in the back segment 18.

FIG. 5c shows a wide portion 22 having a curved shape. The wide portion 22 transitions directly from the remainder of the core 5 to a middle part 36 having a curved shape. The curved shape is for instance part of a circle or an oval. At least the widest part of the curved shape has a width of at least 1.1 times greater than the maximal width W2 in the transverse direction X of the core 5 in the back segment 18. The wide portion 22 transitions directly to a width W4 adjacent the front edge 15 of the core 5 which is narrower than the width W1 of the wide portion 22.

In FIGS. 5a-5c the width W4 of the core 5 adjacent the front edge 15 of the core 5 in the transverse direction X may be smaller than the width of the core 5 in the transverse direction X in the rest of the front segment 17 of the core 5. The width of the core 5 adjacent the front edge 15 of the core 5 in the transverse direction X may be equal to the width of at least part of the core 5 in the rear segment 18 of the core 5 in the transverse direction X.

FIG. 5d shows a wide portion 22 of the core 5 with rounded edges forming the lower transition 34 between the wide portion 22 and the remainder of the core 5 in the bottom part of the wide portion 22. The middle part 36 of the wide portion 22 is essentially straight in a longitudinal direction Y. In this example there are no upper transitions 35 to a narrower width, instead the wide portion 22 maintains its width to the front edge 15 of the core 5.

The length L5 of the wide portion 22 is measured from where the width of the wide portion 22 is at least 1.1 times greater than the maximal width W2 of the rear segment 18. As can be seen from the figures the wide portion 22 can have a greater longitudinal length L5 than the length L1 of the front segment 17 or a smaller longitudinal length L5 than the length L1 of the front segment 17. Additionally, the lower transitions 34 and the upper transitions 35 do not have to have the same shape. Further, the shape of the transitions 34, 35 are mere illustrations and can take other shapes than the ones shown.

The wide portion 22 has an extension in the longitudinal direction Y in the range of 30-200 millimetres, specifically 40-180 millimetres, and more specifically 50-160 millimetres. The wide portion 22 has an extension in the longitudinal direction Y in the range of 20-130%, specifically 25-120%, and more specifically 30-100% of the length L1 of the front segment 17 of the core 5.

The front segment 17 of the core 5 of an absorbent article 1 adapted for males has an area 40 which is at least 1.1 times greater, specifically at least 1.2 times greater than 1.3 times greater than the area 41 of the rear segment 18 of the core 5.

Figure 6:
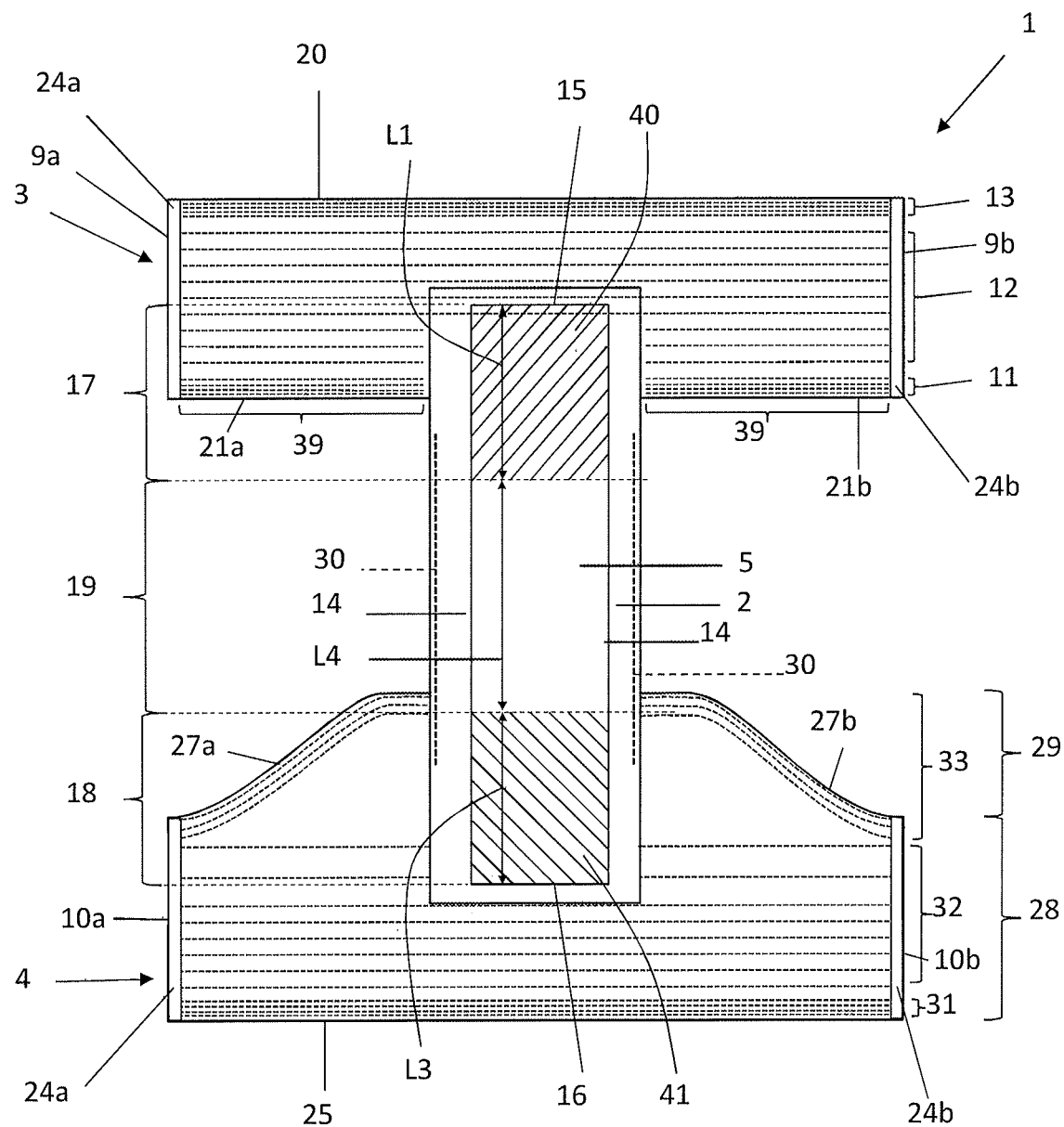
FIG. 6 shows a perspective view of an alternative embodiment of an absorbent article according to the disclosure.

FIG. 6 shows an absorbent article 1 in FIGS. 2 and 3 with an example of how the elastics are arranged in the absorbent article 1. The laminated web material of the front panel 3 comprises a first at least partly elastic region 11 extending along the leg edges 21a, 21b of the front panel 3, thereby defining a leg elastic feature. The laminated web material of the front panel 3 further comprises a second at least partly elastic region 12 located next to the first at least partly elastic region 11 towards the waist edge 20 of the front panel 3. The second at least partly elastic region 12 may be referred to as an elastic belly region because it may, depending on the size of the second at least partly elastic region 12, extend over the belly of a user. The laminated web material of the front panel 3 has a third at least partly elastic region 13 extending primarily in the transverse direction X, being located adjacent the front panel waist edge 20.

The first at least partly elastic region 11 of the front panel 3 may comprise a plurality of elastic threads arranged parallel at substantially equally spaced intervals of for example 2 to 8 millimetres and may for example comprise 4 to 6 elastic threads. Each of the elastic threads may have substantially equal mass density, which for example may lie in the range 600 to 1200 decitex, specifically in the range of 750 to 1000 decitex.

The second at least partly elastic region 12 of the front panel 3 typically corresponds to the belly portion of the absorbent article 1 and may for example comprise a plurality of elastic threads arranged parallel at substantially equally spaced intervals of 5 to 13 millimetres and may for example comprise 9 to 27 elastic threads. Each of the elastic threads may have substantially equal mass density, which for example may lie in the range 350 to 900 decitex, specifically in the range of 500 to 700 decitex. Having relatively large intervals between neighbouring elastic threads in a belly portion in relation to the lower area of the front panel 3 enables a large and comfortable belly portion.

The third at least partly elastic region 13 of the front panel 3 may for example comprise a plurality of elastic threads arranged in parallel at substantially equally spaced intervals of 2 to 8 millimetres and for example comprise 4 to 6 elastic threads. Each of the elastic threads may have substantially equal mass density, which for example may lie in the range 600 to 1200 decitex, specifically in the range of 750 to 1000 decitex.

An upper region 31 of the back panel 4 may for example comprise a plurality of elastic threads arranged parallel at substantially equally spaced intervals of 2 to 8 millimetres and may for example comprise 4 to 6 elastic threads. Each of the elastic threads may have substantially equal mass density, which for example may lie in the range 600 to 1200 decitex, specifically in the range of 750 to 1000 decitex.

A middle region 32 of the back panel 4 may for example comprise a plurality of elastic threads arranged parallel at substantially equally spaced intervals of 5 to 13 millimetres and may for example comprise 7 to 18 elastic threads. Each of the elastic threads may have substantially equal mass density, which for example may lie in the range 350 to 900 decitex, specifically in the range of 500 to 700 decitex.

A lower region 33 of the back panel 4 extending over the buttocks of the user may comprise a plurality of elastic threads arranged parallel at substantially equally spaced intervals of 10 to 30 millimetres and may comprise 3 to 9 elastic threads. Each of the elastic threads may have substantially equal mass density in the range 350 to 900 decitex, specifically in the range of 500 to 700 decitex.

Since it may be advantageous to have the side seams 6a, 6b free from adhesive the continuous elastic threads will in the area of the side seam 6a, 6b during manufacturing of the absorbent article 1 snap back upon the cutting operation required for splitting the continuous material band into individual absorbent articles. Therefore a narrow longitudinal strip 24a, 24b of material is illustrated having no elastic threads attached thereto in FIG. 2. Therefore, the first, second and third elastic regions 11, 12, 13 do not necessarily extend out to the edge 9a, 9b of the front panel 3, as shown in FIG. 2. The same may be done for the back panel 4.

Alternatively, both the front panel 3 and the back panel 4 have a shape composed of a substantially rectangular shaped main section intended to be located towards a waist of a user and a substantially trapezoid shaped section intended to be located towards a crotch of a user. A certain level of variations in said schematic geometry is of course possible. In such an embodiment (not showed) the elasticised region of the first at least partly elastic region 11 may comprise curved portions.

Figure 7:
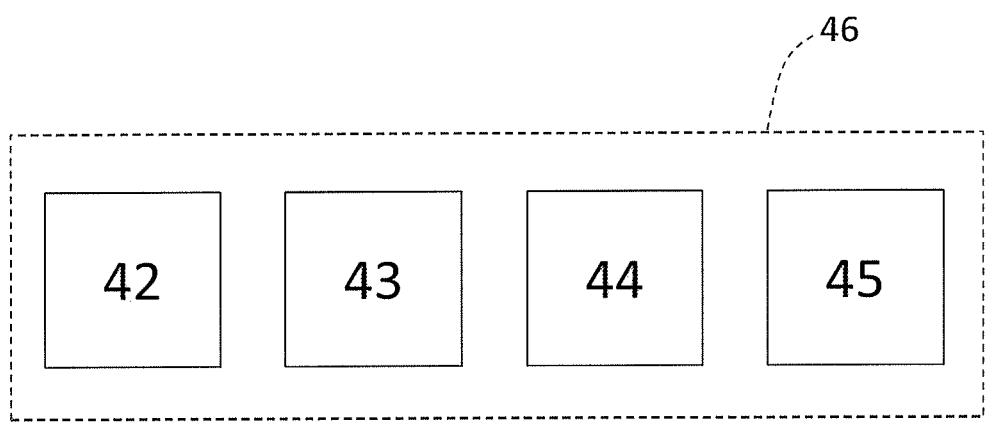
FIG. 7 shows an array of packages comprising absorbent articles of the first and second subarrays.

FIG. 7 shows an array of packages 46 comprising the array 47 of disposable pant-type gender-specific absorbent articles 1. The first subarray 48 of absorbent articles may include a plurality of first size absorbent articles 1 adapted for female users and packed in a first package 42, and a plurality of second size absorbent articles 1 adapted for female users and packed in a second package 43. The second subarray 49 of absorbent articles includes a plurality of third size absorbent articles for male users and packed in a third package 44, and a plurality of fourth size absorbent articles adapted for male users and packed in a fourth package 45. Each of the first to fourth packages 42, 43, 44, 45 in the array of packages 46 comprises an external marking indicating the size and/or suitable gender of the disposable pant-type absorbent articles therein. Such an array can for instance be found in a supermarket or a grocery store selling absorbent articles.

All measurements are made before joining the side edges 9a, 9b, 10a, 10b and making the side seams 6a, 6b of the absorbent article, or with the product cut open at the side seams 6a, 6b, and held flat in an extended and stretched-out state, such that the absorbent article 1 has been extended in both the longitudinal and transverse direction that all the elastics contained therein are extended to such an extent that they no longer gather any part of the product, but the entire absorbent article 1 is completely flat and in an un-gathered state. The article 1 is extended only to such an extent that this flat condition is reached.

By "absorbent article" is meant an article that absorbs or is adapted to absorb bodily fluids, such as urine and/or blood.

The nonwoven material layers or webs of the present disclosure forming the front and back panels may for example be selected from, for example, of spunbond, air laid, wet laid, carded, electro spunned or meltblown nonwovens. The nonwoven material may be bonded by multiple techniques, e.g. by needling, hydroentangling, or heat bonding.

The nonwoven material of the disclosed products is a mixture of natural and synthetic materials. Natural fibres are for instance cellulosic fibres or fibres from regenerated cellulose.

The term "elastic thread" is intended to mean an elastic strand or elastic thread which is made of elastic material, such as e.g. natural or synthetic rubber, thermoplastic elastomers, such as thermoplastic polyurethane or styrene block co-polymers or elastane, also referred as to spandex (polyurethane-polyurea copolymer). The threads may be of the elastane type that is available under the trade name "LYCRA", but any suitable elastic thread may be used. The threads may have a linear mass density, dtex, of about 80-1200 dtex.

The elastic threads are elongated during the production process from about 50 to about 300% of the initial, 'non-tensioned original length, for example may preferably be 100-250% or may preferably be 150-220% of the initial, non-tensioned original length. The elastic threads may preferably be of a type that are able to tolerate an elongation of at least about 200% without breaking, so that they can be safely used in the production process without risk for breaking.

Further information with respect to material about the elastic web material is disclosed in WO2014098683 A1, which is referred to in its entirety.

The absorbent core 5 may comprise any conventional material suitable for absorbing discharged bodily wastes, such as cellulosic fluff pulp, tissue layers, highly absorbent polymers (super absorbents), absorbent foam materials including hydrogel-foam material, absorbent nonwoven materials or the like.

The absorbent core 5 may have a liquid permeable topsheet placed on the side intended to face the skin of a user, and a liquid impermeable backsheet placed on the side of the absorbent body intended to face the garment of a user. Generally, the liquid permeable topsheet comprises or may consist of a nonwoven material. The topsheet material may further be composed of tow fibres, porous foams, apertured plastic films etc. As mentioned above, the materials suited as topsheet materials should be soft and non-irritating to the skin and be readily penetrated by body fluid, e.g. urine or menstrual fluid, and display low rewetting properties.

The liquid impermeable backsheet may consist of a thin plastic film, e. g. a polyethylene or polypropylene film, a nonwoven material coated with a liquid impervious material, a hydrophobic nonwoven material which resists liquid penetration or laminates of plastic films and nonwoven materials. The backsheet material may be breathable so as to allow vapour to escape from the absorbent body, while still preventing liquids from passing through the backsheet material.

The topsheet and backsheet may be connected to each other for example by adhesive bonding, gluing or welding by heat or ultrasonic. The topsheet and/or the backsheet may further be attached to the absorbent body by any method known in the art, such as adhesive, heat-bonding etc.

The topsheet and backsheet of the absorbent core 5 may extend outwardly beyond the area of the absorbent core 5, thereby defining an absorbent insert 2 comprising an absorbent core 5. The maximal width of the absorbent core 5 is typically about 80 to 150 mm in transverse direction X, and the maximal length L6 of the absorbent core 5 is typically and 400 to 600 mm in longitudinal direction Y.

The absorbent core 5 may overlap the front panel 3 with a length of about 50-100 mm. Moreover, the absorbent core 5 may overlap the body panel 4 with a length of about 200-250 mm; alternatively, the absorbent core 5 may overlap the main section 28 of the back panel 4 with a length of about 30-70 mm.

Reference signs mentioned in the claims should not be seen as limiting the extent of the matter protected by the claims, and their sole function is to make claims easier to understand.

As will be realised, the disclosure is capable of modification in various obvious respects, all without departing from the scope of the appended claims. Accordingly, the drawings and the description thereto are to be regarded as illustrative in nature, and not restrictive. It should be understood that the present absorbent articles and its components and methods are not intended to be limited to the particular forms disclosed. Rather, they are intended to include all modifications, equivalents, and alternatives falling within the scope of the claims. They are further intended to include embodiments that may be formed by combining features from the disclosed embodiments, and variants thereof.

FEATURES

1. Absorbent article
2. Absorbent insert
3. Front panel
4. Back panel
5. Absorbent core
6. Side seams (a, b)
7. Waist opening
8. Leg opening
9. Front panel side edges (a, b)
10. Back panel side edges (a, b)
11. First at least partly elastic region
12. Second at least partly elastic region
13. Third at least partly elastic region
14. Longitudinal core edges
15. Front core edge
16. Back core edge
17. Front segment
18. Back segment
19. Middle segment
20. Front panel waist edge
21. Front panel leg edges (a, b)
22. Wide portion
23. Transverse centre line
24. Longitudinal strip
25. Back panel waist edge
27. Back panel leg edges (a, b)
28. Back panel main section
29. Back panel trapezoid section
30. Side elastic members
31. Upper region
32. Middle region
33. Lower region
34. Lower transition
35. Upper transition
36. Middle part
37. Front panel main section
38. Front panel trapezoid section
40. Front core area
41. Back core area
42. First package
43. Second package
44. Third package 45. Fourth package
46. Array of packages
47. Array
48. First subarray
49. Second subarray
50. Back edge of absorbent insert
W1 Width of front segment
W2 Maximal width of core in back segment
W3 Limit width defining wide portion
W4 Width of core adjacent the front edge
W5 Width of absorbent insert
W6 Width of front panel
L1 Length of front segment
L2 Length of back segment
L3 Length of middle segment
L4 Longitudinal length of side elastic members extending between the transverse centre line of the absorbent article towards the front core edge
L5 Length of wide portion
L6 Length of the absorbent core
L7 Total longitudinal length of side elastic member
L8 Length of absorbent insert
L9 Total length of article
L10 Distance from waist edge of the front panel to transverse centre line
L11 Longitudinal length between the transverse centre line of the absorbent article and the back core edge of the absorbent insert
L12 Smallest longitudinal distance between front and back panel

The invention claimed is:

1. An array of disposable pant-type gender-specific absorbent articles adapted for female and male users, the array comprises:
a first subarray of absorbent articles including a first size absorbent article adapted for female users and a second size absorbent article adapted for female users, wherein the second size is larger than the first size,
a second subarray of absorbent articles including a third size absorbent article adapted for male users and a fourth size absorbent article adapted for male users, wherein the fourth size is larger than the third size,
wherein each absorbent article of the array has a longitudinal direction (Y) and a transverse direction (X) and comprises:
a front panel having a front waist edge, a pair of front leg edges and a pair of front side edges,
a back panel having a back waist edge, a pair of back leg edges, and a pair of back side edges,
an absorbent insert located mainly in a crotch portion of each absorbent article and the absorbent insert being connected to the front panel and the back panel and the absorbent insert having an absorbent core with longitudinal core edges, a front core edge and a back core edge, and the insert comprising a topsheet and backsheet,
wherein each absorbent core in each absorbent article in the array of absorbent articles has a front portion extending in the longitudinal direction (Y) from a transverse centre line of each absorbent article to the front core edge and defining a front core area, and a back portion extending in the longitudinal direction (Y) from the transverse centre line of each absorbent article to the back core edge and defining a back core area,
wherein each absorbent article in the array of absorbent articles has side elastic members located underneath the topsheet and extending along the longitudinal core edges,
wherein each absorbent article in the first subarray has a front core area-to-back core area ratio less than 1.2,
wherein each absorbent article in the second subarray has a front core area-to-back core area ratio larger than 1.2, and
wherein a longitudinal length of a portion of the side elastic members extending between the transverse centre line towards the front core edge of each absorbent article of the first subarray is smaller than a longitudinal length of a portion of the side elastic members extending between the transverse centre line towards the front core edge of each absorbent article of the second subarray.

2. The array of disposable pant-type gender-specific absorbent articles according to claim 1, wherein a width of the front panel in the transverse direction (X) of each absorbent article of the first subarray is substantially the same as a width of the front panel in the transverse direction (X) of each absorbent article of the second subarray.

3. The array of disposable pant-type gender-specific absorbent articles according to claim 1, wherein the longitudinal length of the portion of the side elastic members extending between the transverse centre line towards the front core edge of each absorbent article of the first subarray is at least 15% shorter than the longitudinal length of the portion of the side elastic members extending between the transverse centre line towards the front core edge of each absorbent article of the second subarray.

4. The array of disposable pant-type gender-specific absorbent articles according to claim 1, wherein a total longitudinal length of the side elastic members of each absorbent article of the first subarray is at least 15% shorter than a total longitudinal length of the side elastic members of each absorbent article of the second subarray.

5. The array of disposable pant-type gender-specific absorbent articles according to claim 1, wherein each absorbent core in the array has a front segment with a length in the longitudinal direction (Y) which is 30% of the total length of the core in the longitudinal direction (Y) and extending from the front core edge, wherein the front core area of the front segment of each absorbent article in the second subarray is at least 1.1 times larger than the front core area of the front segment of each absorbent article in the first subarray.

6. An array of disposable pant-type gender-specific absorbent articles adapted for female and male users, the array comprises:
a first subarray of absorbent articles including a first size absorbent article adapted for female users and a second size absorbent article adapted for female users, wherein the second size is larger than the first size,
a second subarray of absorbent articles including a third size absorbent article adapted for male users and a fourth size absorbent article adapted for male users, wherein the fourth size is larger than the third size,
wherein each absorbent article of the array has a longitudinal direction (Y) and a transverse direction (X) and comprises:
a front panel having a front waist edge, a pair of front leg edges and a pair of front side edges,
a back panel having a back waist edge, a pair of back leg edges, and a pair of back side edges, an absorbent insert located mainly in a crotch portion of each absorbent article and the absorbent insert being connected to the front panel and the back panel and the absorbent insert having an absorbent core with longitudinal core edges, a front core edge and a back core edge, wherein each absorbent core in each absorbent article in the array of absorbent articles has a front portion extending in the longitudinal direction (Y) from a transverse centre line of each absorbent article to the front core edge and defining a front core area, and a back portion extending in the longitudinal direction (Y) from the transverse centre line of each absorbent article to the back core edge and defining a back core area, wherein each absorbent article in the array of absorbent articles has side elastic members extending along the longitudinal core edges, wherein each absorbent article in the first subarray has a front core area-to-back core area ratio less than 1.2, wherein each absorbent article in the second subarray has a front core area-to-back core area ratio larger than 1.2, and wherein a longitudinal length of a portion of the side elastic members extending between the transverse centre line towards the front core edge of each absorbent article of the first subarray is smaller than a longitudinal length of a portion of the side elastic members extending between the transverse centre line towards the front core edge of each absorbent article of the second subarray, wherein a smallest longitudinal distance between a side edge of the front panel and an oppositely located side edge of the back panel of each absorbent article in the array is essentially the same.

7. The array of disposable pant-type gender-specific absorbent articles according to claim 1, wherein at least one of a size of the absorbent insert in the longitudinal direction (Y) and a size of the absorbent insert in the transverse (X) direction is the same for all absorbent articles in the array.

8. The array of disposable pant-type gender-specific absorbent articles according to claim 1, wherein all absorbent articles within the first subarray have substantially identical absorbent inserts, and wherein all absorbent articles within the second subarray have substantially identical absorbent inserts.

9. The array of disposable pant-type gender-specific absorbent articles according to claim 1, wherein each absorbent article in the array has a substantially equal longitudinal length between the transverse centre line of the absorbent article and a back edge of the absorbent insert to each of the other absorbent articles in the array.

10. The array of disposable pant-type gender-specific absorbent articles according to claim 1, wherein the front panel and the back panel of each absorbent article in the array are joined to each other by seams at opposite side edges by seams forming to form a waist opening and two leg openings in each absorbent article.

11. The array of disposable pant-type gender-specific absorbent articles according to claim 1, wherein a maximal width of the absorbent core of each absorbent article in the array is between 120 and 200 mm in the transverse direction (X) and wherein a minimal width of the absorbent core of each absorbent article in the array is between 60 and 140 mm in the transverse direction (X).

12. The array of disposable pant-type gender-specific absorbent articles according to claim 1, wherein, for each absorbent article in the array, a front portion of the absorbent insert is attached to the front panel of the absorbent article and a back portion of the absorbent insert is attached to the back panel of the absorbent article.

13. The array of disposable pant-type gender-specific absorbent articles according to claim 1, wherein at least one of the front and back panel of each absorbent article in the array comprises an elastic web material that is elasticized in the width direction, wherein the elastic web material that is elasticized in the width direction comprises at least two inelastic sheets of web material laminated together and having an elastic feature sandwiched between said at least two inelastic sheets of web material, and wherein the elastic feature is attached to the at least two inelastic sheets of web material in a tensioned state in the width direction to provide the elastic web material that is elasticized in the width direction.

14. The array of disposable pant-type gender-specific absorbent articles according to claim 13, wherein the elastic feature of each absorbent article in the array comprises an elastic film extending both in the length direction and width direction, or a plurality of substantially parallel elastic threads.

15. The array of disposable pant-type gender-specific absorbent articles according to claim 1, wherein the front panel and the back panel of each absorbent article in the array both comprise individual parts that are all mutually interconnected by means of the absorbent insert, or wherein the front panel and the back panel are both integral parts of a single-piece chassis comprised of one piece of web material having cut-out leg openings, wherein the absorbent body is located overlapping a crotch portion of the chassis.

16. The array of disposable pant-type gender-specific absorbent articles according to claim 1, wherein the absorbent articles in the array are pant diapers or sanitary pants or incontinence pants.

17. An array of packages comprising the array of disposable pant-type gender-specific absorbent articles according to claim 1, wherein the first subarray of absorbent articles includes a plurality of the first size absorbent articles adapted for female users packed in a first package, and a plurality of the second size absorbent articles adapted for female users packed in a second package, wherein the second subarray of absorbent articles includes a plurality of the third size absorbent articles for male users packed in a third package, and a plurality of the fourth size absorbent articles adapted for male users packed in a fourth package, wherein each of the first, second, third, and fourth packages in the array of packages comprises an external marking indicating at least one of the size and the suitable gender of the disposable pant-type absorbent articles therein.

18. The array of disposable pant-type gender-specific absorbent articles according to claim 1, wherein the side elastic members are configured to have a gathering effect on long sides of the front portion of the absorbent core, such that the absorbent core within a region of the side elastic members contracts in the direction of extension of the side elastic members.

19. The array of disposable pant-type gender-specific absorbent articles according to claim 18, wherein the absorbent core contracts in a manner to shape the absorbent core in the absorbent article, such that in the first subarray the shaping of the absorbent core is configured for female users, and such that in the second subarray the shaping of the absorbent core is configured to form an outward bulge of the absorbent core in the area of male genitals.

20. The array of disposable pant-type gender-specific absorbent articles according to claim 1, wherein a smallest longitudinal distance between a side edge of the front panel and an oppositely located side edge of the back panel of each absorbent article in the array is essentially the same.

* * * * *